US00PP12723P2

(12) United States Plant Patent
Zerr

(10) Patent No.: US PP12,723 P2
(45) Date of Patent: Jun. 25, 2002

(54) POINSETTIA PLANT NAMED 'FISCOR DARK RED'

(75) Inventor: Katharina Zerr, Höhr-Grenzhausen (DE)

(73) Assignee: Floris AG, Binningen (CH)

( * ) Notice: Subject to any disclaimer, the term of this patent is extended or adjusted under 35 U.S.C. 154(b) by 0 days.

(21) Appl. No.: 09/496,196

(22) Filed: Feb. 2, 2000

(51) Int. Cl.[7] ..... A01H 5/00
(52) U.S. Cl. ..... Plt./307
(58) Field of Search ..... Plt./307, 303

(56) References Cited

U.S. PATENT DOCUMENTS

PP6,592 P * 2/1989 Gross ..... Plt./307
PP9,106 P * 4/1995 Jacobsen ..... Plt./307
PP9,364 P * 11/1995 Zerr ..... Plt./307

OTHER PUBLICATIONS

German Application for 'FISCOR DARK RED' (Dec. 15, 1998).
German Denomination for 'FISCOR DARK RED' (Mar. 15, 1999).
Plant Varieties Journal, No. 31 (Apr. 1999), pp. 40–41 (Canada).

* cited by examiner

*Primary Examiner*—Bruce R. Campell
*Assistant Examiner*—June Hwu
(74) *Attorney, Agent, or Firm*—Foley & Lardner

(57) ABSTRACT

A new and distinct cultivar of Poinsettia plant named 'Fiscor Dark Red' characterized by having dark-red bract color; medium-sized, almost flat inflorescence with weakly lobed bracts; intense dark-green foliage with slight dentation; compact and wide, lowly molded plant habit; medium to late flowering response; and relatively good keeping quality of bracts and foliage.

1 Drawing Sheet

BACKGROUND OF THE INVENTION

The present invention relates to a new and distinct cultivar of poinsettia plant known by the cultivar name 'Fiscor Dark Red' and botanically known as *Euphorbia pulcherrima*.

'Fiscor Dark Red' is a product of a mutation induction program carried out by the inventor, Katharina Zerr, in Hillscheid, Germany, in 1994. The primary objective of the induction program was to expand the bract color ranges of 'Fiscor' (U.S. Plant Pat. No. 9,364). 'Fiscor' is characterized by its relatively dark red-colored bracts, dark-green foliage and comparatively compact plant habit.

The irradiation program comprised exposing rooted cuttings taken from plants of the parent cultivar to an X-ray source of 30 Gy dosage in Ahrensburg, Germany, under the supervision of the inventor. The irradiated plants were grown out in a greenhouse in Hillscheid, Germany, and were asexually propagated by the inventor by taking cuttings. The plants resulting from these cuttings were screened for mutations as small, flowering, single-stem plants beginning in fall of 1994. The mutations discovered were identified by numbers. Parts of plants exhibiting a mutation of interest were left to develop vegetative shoots which were used as cuttings and grown out.

'Fiscor Dark Red' originated from a single plant (no. 222) having a distinctly darker-red bract color, which was discovered in the spring of 1995. This plant, which appeared to be completely mutated, was propagated vegetatively by taking cuttings, and the off-spring were screened for uniformity in the spring of 1996 prior to further propagation. The clone was examined more closely in autumn of 1997, and again in the late summer and autumn of 1998 in Hillscheid, Germany. Horticultural examination of the clone starting in 1997 and continuing thereafter has confirmed that the combination of characteristics as herein disclosed for 'Fiscor Dark Red' are firmly fixed and retained through successive generations of asexual reproduction.

BRIEF DESCRIPTION OF THE INVENTION

The following traits have been repeatedly observed and are determined to be basic characteristics of 'Fiscor Dark Red' which in combination distinguish this Poinsettia as a new and distinct cultivar:

1. Dark-red bract color;
2. Medium-sized, almost flat inflorescence with weakly lobed bracts;
3. Intense dark-green foliage with slight dentation;
4. Compact and wide, lowly molded plant habit;
5. Medium to late flowering response; and
6. Relatively good keeping quality of bracts and foliage.

'Fiscor Dark Red' has not been observed under all possible environmental conditions. The phenotype may vary significantly with variations in environment such as temperature, light intensity, and daylength without any change in genotype. The following observations, measurements and comparisons describe plants grown in Langley, British Columbia, Canada, under greenhouse conditions which approximate those generally used in commercial practice.

Of the many commercial cultivars known to the inventor, the most similar in comparison to 'Fiscor Dark Red' are the parent cultivar 'Fiscor' and the co-pending cultivar 'Fisson Dark Red' (U.S. Plant patent application Ser. No. 09/496,459). In comparison to 'Fiscor', 'Fiscor Dark Red' has a considerably darker red bract color, slightly narrower bracts and leaves, and even more intense anthocyanin coloration of stems and petioles.

In comparison to 'Fisson Dark Red', 'Fiscor Dark Red' has differently shaped inflorescence with flat, not folded, and relatively smooth-surfaced bracts. 'Fiscor Dark Red' has a wider but shorter plant habit than 'Fisson Dark Red'.

BRIEF DESCRIPTION OF THE DRAWING

The accompanying color photographic illustration shows typical inflorescence and foliage of a mature potted plant of 'Fiscor Dark Red', with colors being as true as possible with illustrations of this type.

DETAILED BOTANICAL DESCRIPTION

The plants described were grown in a greenhouse in Langley, British Columbis, Canada, in the fall of 1998. Rooted cuttings were planted into 15-cm pots (in diameter) on August 10, and were pinched on August 20, leaving 8 nodes. The minimum temperature was 23° C. until October 10, 20° C. to mid-November, and lower thereafter. The plants initiated flowers under natural short-day conditions in the fall. The following measurements were made on Nov. 24–25, 1998, 15 weeks after planting of rooting cuttings. Additional observations were made in Hillscheid, Germany, in early December using 17 week old plants of similar size.

Observations and measurements were mainly taken at the beginning of flowering. In the following description, color references are made to The Royal Horticultural Society (R.H.S.) Color Chart. The color values were determined indoors in a north light.

Classification:

*Botanical.*—*Euphorbia pulcherrima.*

*Commercial.*—Poinsettia cv. Fiscor Dark Red.

Parentage: Induced mutation of 'Fiscor'.

Plant:

*Form.*—Shrub, self-branching.

*Growth habit.*—Moderately compact under natural short-day conditions in the fall, weak to medium growth, pinched plants are bushy and round in shape.

*Height* (*including 12 cm high pot*).—Approximately 40.3 cm.

*Width.*—51.0 cm.

*Average number of branches.*—10.3.

*Stem color.*—Brownish-purple, approximately RHS 184A, caused by very strong infusion of anthocyanin.

*Peduncle.*—Light green to green, RHS 143A to RHS 143B, about 6 mm long.

*Rooting.*—Medium, sufficiently rooted for transplanting after about 20 days in a greenhouse at a temperature of 22–24° C.

*Blooming habit.*—Flowering response time under natural short day conditions in autumn: botanically (cyathia open)— in early December; commercially (bracts colored, marketable)— in early December.

*Flowering response time.*—About 10 weeks.

Foliage:

*Shape.*—Ovate with acute to rounded base, acuminate tip.

*Margin.*—Entire, with irregular crenation in parts.

*Texture.*—Upper surface: Smooth, flat and only weakly veined; color of veins is about RHS 180A or lighter; the basal part of the midrib has an almost similar dark-red coloring as the petiole. Lower surface: Flat and smooth except for the slightly protruding midrib and finer side veins, which are arranged in a pinnate pattern. The vein color is light-green, RHS 145B; the basal part of the midrib has a weak infusion of anthocyanin.

*Size.*—Leaf blade length is 12.2 cm; leaf blade width is 7.5 cm; petiole length is 7.5 cm.

*Color.*—Generally a uniform dark-green. Mature foliage: Upper surface is RHS 139A. Under surface is RHS 137A–B. New foliage: Upper side is about RHS 143A. Under side is about RHS 137D.

*Petiole color.*—Dark-red, RHS 53A to RHS 185A.

*Aspect.*—Petioles and leaves are horizontally directed.

*Disease resistance.*—Typical, no special observations made.

Flowering description:

*Whole inflorescence.*—Almost flat and horizontally directed, with the bracts in a slightly overlapping arrangement.

*Keeping quality of the bracts.*—Relatively good.

*Diameter of inflorescence.*—23 cm.

*Number of bracts per inflorescence.*—8–11 bracts (with a length over 2 cm).

*Size of bract.*—Largest true bract is 12.7 cm long and 9.3 cm wide; petiole is 2.0 cm.

*Bract shape.*—Ovate with rounded to acute base, acuminate tip, and weak dentation; the smaller, younger bracts are elliptically shaped and usually without lobes.

*Bract texture.*—Flat and only slightly rugose; the pattern of the veins is the same as that of the leaves. The veins are hardly visible on the upper surface and their color corresponds to the bract color or appears slightly darker, while the veins on the lower surface usually lighter; pink, about RHS 46D.

*Bract color.*—Generally a uniform dark-red, without tendency to fading near the margin, nor at high temperature. Upper surface: Near RHS 46A–B, the younger bracts are RHS 46A. Lower surface: RHS 46B.

*Secondary bract.*—Elliptical shape, acute base, weak or no development of lobes, upper surface between Near RHS 46A–B, lower surface RHS 46B; largest secondary bract 12.7 cm long, next largest secondary bract 9 cm long and 5.5–6 cm wide.

*Petiole color.*—Reddish, about RHS 46A–B.

*Cyme.*—About 20–25 mm wide, few cyathia, about 10 in a narrow cluster. Diameter of a single cyathium: 5–6 mm. Color: Mainly light to medium green, RHS 143B; the top has a small, star-shaped pattern, red, RHS 46A–B. Retention: Average. Nectar Cups: Usually one nectar cup per cyathium, small to medium sized, 4–5 mm diameter, 4 mm length, golden yellow, RHS 12A, anthocyanin coloring may occur near the margin, orange-red near RHS 40 A.

Reproductive organs:

*Stamens.*—Approximately 20 in a cluster, dark-red filaments, RHS 46A, fertile, yellow pollen, RHS 8 A.

*Pistils.*—One pistil per cyathium, style and stigma are dark-red, near RHS 46A; 6-lobed stigma, trifuracte.

*Ovaries.*—Triangular, 3 ovules.

Fruit/seed set: No observations made.

I claim:

1. A new and distinct poinsettia plant named 'Fiscor Dark Red', substantially as illustrated and described.

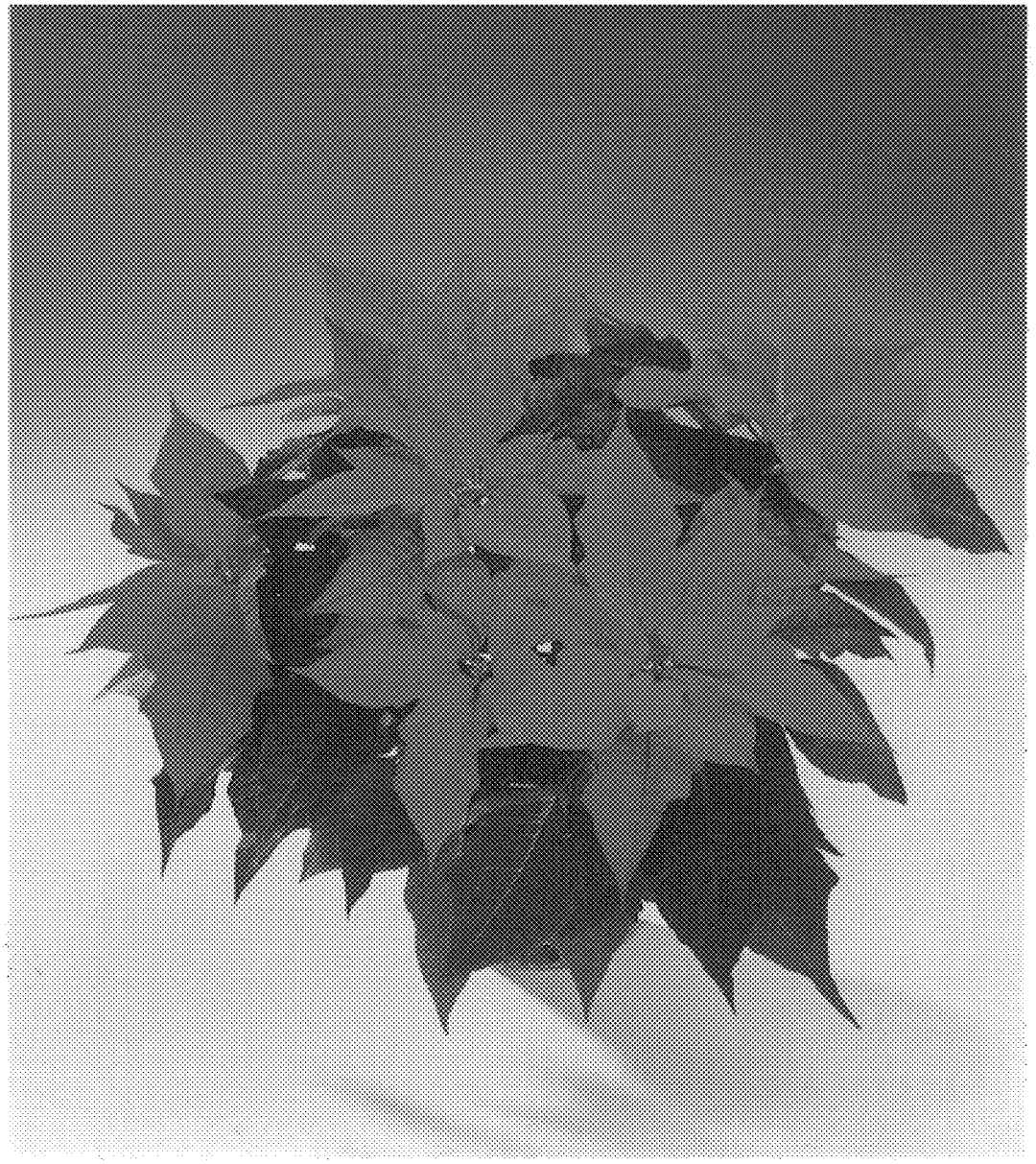

* * * * *